(12) United States Patent
Gerhardt et al.

(10) Patent No.: US 11,116,434 B2
(45) Date of Patent: Sep. 14, 2021

(54) SEGMENTED ELCTRODE

(71) Applicant: KONINKLIJKE PHILIPS N.V., Eindhoven (NL)

(72) Inventors: Lutz Christian Gerhardt, Eindhoven (NL); Neil Francis Joye, Waalre (NL); Mark Thomas Johnson, Arendonk (BE); Mohammed Meftah, Tilburg (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 176 days.

(21) Appl. No.: 16/095,729

(22) PCT Filed: Oct. 16, 2017

(86) PCT No.: PCT/EP2017/076353
§ 371 (c)(1),
(2) Date: Oct. 23, 2018

(87) PCT Pub. No.: WO2018/073174
PCT Pub. Date: Apr. 26, 2018

(65) Prior Publication Data
US 2020/0329992 A1    Oct. 22, 2020

(30) Foreign Application Priority Data
Oct. 18, 2016 (EP) ..................... 16194297

(51) Int. Cl.
*A61B 5/0402* (2006.01)
*A61B 5/282* (2021.01)
(Continued)

(52) U.S. Cl.
CPC .............. *A61B 5/282* (2021.01); *A61B 5/259* (2021.01); *A61B 5/721* (2013.01); *A61B 5/0077* (2013.01);
(Continued)

(58) Field of Classification Search
CPC ... A61B 5/0412; A61B 5/0245; A61B 5/0408; A61B 5/053; A61B 5/04085;
(Continued)

(56) References Cited

U.S. PATENT DOCUMENTS

| 5,445,537 A | 8/1995 | Abyzov |
| 5,724,984 A | 3/1998 | Arnold et al. |

(Continued)

FOREIGN PATENT DOCUMENTS

| WO | 2000061001 A1 | 10/2000 |
| WO | 2015107339 A1 | 7/2015 |
| WO | 2016076975 A1 | 5/2016 |

OTHER PUBLICATIONS

Ko, et al., "Motion Artifact Reduction in Electrocardiogram using Adaptive Filtering Based on Half Cell Potential Monitoring", 34th Annual International Conference of the IEEE EMBS, San Diego, California USA, Aug. 28-Sep. 1, 2012pp. 1590-1593.

(Continued)

*Primary Examiner* — Joseph A Stoklosa
*Assistant Examiner* — Brian M Antiskay

(57) ABSTRACT

Disclosed is a vital sign monitoring system. The system comprises a segmented electrode forming an in-plane electrode array, wherein the electrode comprise a skin contacting skin adhering contact layer mounted on an electrode backing material, a deformation sensor arranged for identifying deformation information of the electrode, a signal processor arranged to receive a vital sign signal from the electrode and process the deformation information to remove artefacts from the vital sign signal, wherein the electrode comprises multiple electrode segments and wherein the signal processor is arranged to select that electrode segment that has a lowest deformation of all electrode segments of the electrode.

20 Claims, 5 Drawing Sheets

(51) Int. Cl.
*A61B 5/00* (2006.01)
*A61B 5/259* (2021.01)

(52) U.S. Cl.
CPC . *A61B 2562/028* (2013.01); *A61B 2562/0217* (2017.08); *A61B 2562/0223* (2013.01); *A61B 2562/0266* (2013.01); *A61B 2562/046* (2013.01)

(58) Field of Classification Search
CPC ... A61B 5/0006; A61B 5/0428; A61B 5/0402; A61B 5/11; A61B 5/721; A61B 5/6831; A61B 2562/046; A61B 5/04017; A61B 5/0404; A61B 5/6804; A61B 5/7225; A61B 2562/164; A61B 5/6833; A61B 2562/04
USPC .......................... 600/372, 382–393, 508–509
See application file for complete search history.

(56) References Cited

U.S. PATENT DOCUMENTS

| | | | |
|---|---|---|---|
| 5,978,693 | A | 11/1999 | Hamilton et al. |
| 6,912,414 | B2 | 6/2005 | Tong |
| 2005/0010121 | A1* | 1/2005 | Ross ............... A61B 5/0428 600/509 |
| 2009/0018428 | A1 | 1/2009 | Dias et al. |
| 2009/0177073 | A1 | 7/2009 | Sonnenborg |
| 2010/0041975 | A1* | 2/2010 | Chen ............... A61B 5/04085 600/393 |
| 2011/0230749 | A1* | 9/2011 | Chan ............... A61B 5/0408 600/393 |
| 2013/0150697 | A1 | 6/2013 | Imai et al. |
| 2014/0031895 | A1 | 1/2014 | Rahimi et al. |
| 2016/0029960 | A1 | 2/2016 | Toth et al. |
| 2016/0296135 | A1 | 10/2016 | Yoo et al. |

OTHER PUBLICATIONS

Kearney, et al., "Quantification of Motion Artifact in ECG Electrode Design", Proceedings of the 29th Annual International Conference of the IEEE EMBS, Cité Internationale, Lyon, France, Aug. 23-26, 2007, pp. 1533-1536.
Talhouet, et al., "The origin of skin-stretch-caused motion artifacts under electrodes", Physiol. Meas. 17 (1996), pp. 81-93. Printed in the UK.
Obropta, et al., "A comparison of human skin strain fields of the elbow joint for mechanical counter pressure space suit development", 2015 IEEE Aerospace Conference, Mar. 7-14 2015, Big Sky, MT, US, pp. 1-9.
Goverdovsky, et al., "Co-Located Multimodal Sensing: A Next Generation Solution for Wearable Health", IEEE Sensors Journal, vol. 15, No. 1, Jan. 2015, pp. 138-145.
Kim, et al., "A 2.4µA Continuous-time Electrode-Skin Impedance Measurement Circuit for Motion Artifact Monitoring in ECG Acquisition Systems", 2010 IEEE Symposium on VLSI Circuits/ Technical Digest of Technical Papers, pp. 219-220.
Smith, M., "Rx for ECG Monitoring Artifact", 3 pages (Abstract).
Pengjun, et al., "Measurement of Wearable Electrode and Skin Mechanical Interaction Using Displacement and Pressure Sensors", IEEE 2011 4th International Conference on Biomedical Engineering and Informatics (BMEI), pp. 1131-1134.
Liu, et al., "Reduction of Skin Stretch Induced Motion Artifacts in Electrocardiogram Monitoring Using Adaptive Filtering", Proceedings of the 28th IEEE EMBS Annual International Conference New York City, USA, Aug. 30-Sep. 3, 2006, pp. 6045-6048.
Yoon, et al., "Adaptive Motion Artifacts Reduction Using 3-axis Accelerometer in E-textile ECG Measurement System", J Med Syst (2008) 32: pp. 101-106.
S. Ödman, et al., "Movement-induced potentials in surface electrodes, Medical and Biological Engineering and Computing", 1982, 20:159, https://link.springer.com/article/10.1007%2FBF02441351 (Abstract).

* cited by examiner

SEGMENTED ELCTRODE

This application is the U.S. National Phase application under 35 U.S.C. § 371 of International Application No. PCT/EP2017/079514, filed on Oct. 16, 2017, which claims the benefit of European Application Serial No. 16194297.4, filed Oct. 18, 2016. These applications are hereby incorporated by reference herein.

FIELD OF THE INVENTION

The present invention relates to a vital sign measurement system and method in the wearable technology.

BACKGROUND OF THE INVENTION

The rising trend in ageing population, increases attention to health and well-being and growing domain of at-home monitoring.

For example the Philips' Biosensor patch enables continuous home monitoring of vital signs such as ECG, heart rate, respiration rate, skin temperature and activity. The clinical data is sent to and processed by a cloud based platform and supports the healthcare professionals in their clinical decision making. The Biosensor patch can prevent hospital readmissions by detecting health deterioration in the home setting as early as possible.

Increase of physician and patient acceptance of such devices, however, requires device optimization.

One of the most important vital signs is the ECG (ElectroCardioGram). The electrical activity of the heart is sensed by monitoring electrodes placed on the skin surface. The electrical signal is very small (normally 0.1 to 3 mV). These signals are within the frequency range of 0.05 to 100 Hertz. Unfortunately, artefact signals of similar frequency and often larger amplitude can reach the skin surface and mix with the ECG signals. Artefact signals arise from several internal and external sources. Internal or physiologic sources of artefact are: signals from other muscles (electromyographic signals) and signals produced in the epidermis. External or non-physiologic sources of artefact are: 50 Hz pickup, offset signals produced by the electrode itself, signals produced by the interaction of body fluids and the electrode gel, and lead wire and patient cable problems, general motion artefacts due to random body movements or bad electrode-to-skin adhesion.

Skin (epidermis) stretching is the primary source of movement-related artefacts in vital body signs measurements (mainly electrical, but also optical, chemical). Studies have revealed that a voltage of several millivolts can be generated by stretching the epidermis, the outer layer of the skin. Compared to the intrinsic, inherent natural strain (skin is under pre-tension), skin surface strains can become as high as 30-50% when skin is externally loaded or stretched. This type of artefact is for instance visible as large baseline shifts and recurrent drifts in the ECG signal occurring when the patient changes positions in bed, eats or walks around. The epidermal artefact is the most troublesome of all movement related artefacts because it is difficult to filter electronically and its amplitude is often larger than the ECG signal. The most obvious solution to avoid motion related artefacts is doing the measurement in a 'still' position by ensuring that the patient does not move during the measurements. This is in practice however often not possible, especially in diseased patients suffering from Parkinson (tremor), or when vital signs should be monitored continuously 24/7 or during exercise/sports. Therefore many attempts have been made to correct for motion artefacts by sophisticated software algorithms and adaptive filtering, using multiple electrodes or additional sensing modalities such as pressure, displacement, microphones, or optical sensors, accelerometers, skin impedance measurement integrated in the electrode to obtain contextual information or to correct for skin strain induced motion artefacts based on the detected amount of motion.

U.S. Pat. No. 6,912,414 B2 for instance discloses an electrode system for reducing noise from an electronic signal, the system including an electrode that provides the electronic signal, and a motion sensor that senses motion and provides a motion signal. The electrode system includes a controller that determines a noise value based on an analysis of the motion signal, and subtracts the noise value from the electronic signal. The electrode system can reduce or eliminate motion artefact from an electronic signal thus avoiding misdiagnosis, prolong procedural duration and inappropriate treatment of a patient.

The drawback of this solution is the following: it involves complicated algorithms to subtract noises from measurement signal only after measurement of the patient.

SUMMARY OF THE INVENTION

It is an object of the present invention to optimize the monitoring of vital signs of a patient and reduce/minimize skin stretching based signal artefacts.

According to a first aspect of the invention, this object is realized by a vital sign monitoring system. The system comprises a segmented (and, for example, stretchable) electrode forming an in-plane electrode array (for example, arranged to allow for accommodating to skin-electrode strain mismatch and strain measurement), wherein the electrode comprises a skin adhering contact layer (for example, a skin contacting adhering layer) mounted on a skin facing side of the electrode, a deformation sensor arranged for identifying a deformation information of the electrode and/or underlying skin, a signal processor arranged to receive a vital sign signal from the electrode and process the deformation information to remove artefacts from the vital sign signal, wherein the segmented electrode comprises multiple electrode segments and wherein the signal processor is arranged to select that electrode segment that has a lowest deformation of all electrode segments of the electrode.

The invention achieves the objective by selecting one or more electrode segments that have the lowest (skin and/or electrode) deformation for measurement thus selecting the signal with the least amount of artefacts from the multi-segmented electrode. The effect of deformation is therefore greatly reduced before sampling, thereby simplifying, or even removing the need for, the signal processing trying to compensate for the artefacts after sampling.

In various embodiments, the signal processor may be arranged to measure the vital sign signal using the selected electrode segment.

In various embodiments, the electrode may comprise either (semi-) rigid or stretchable, flexible sheet of material arranged to support the multiple electrode segments with respect to each other.

In various embodiments, the skin facing side of the electrode may comprise an electrode backing material. In various embodiments, the electrode backing material may comprise the multiple electrode segments. In various embodiments, the electrode may comprise either (semi-) rigid or stretchable, flexible sheet of material as the backing material.

A continuous measurement of skin deformation and analyzing the local skin strain field/strain distribution under the skin contacting electrode by the deformation sensor allows the selection of an electrode segment with little deformation. For example: a stretchable radially arrayed electrode has one or more integrated micro-cameras allowing one to track skin deformation and derive associated strains using digital image correlation. The micro-camera or electrode may have an additional light source to project random patterns onto the skin or a transparent skin adhesive to be able to improve image correlation quality. Using suitable data acquisition and image correlations algorithms and control loops (multiplexing) one can continuously measure local in-plane strains and switch between electrode segments to adapt to changing skin strain fields (body motion, or induced skin stretching), and read out electrode segments associated with lines of non-extension (LoNE) to obtain 'deformation free' vital sign signal.

The electrode are stick-to skin electrodes but also other sensing electrode types (dry electrodes, textile electrodes, wet electrode) will benefit from the proposed deformation measurement and electrode segmentation. A deformation (skin extension) measurement and analysis enable to always select the best segment(s) to use to read out signals with the least amount of skin stretching associated artefacts. This makes especially sense in stretch critical measurements, but having many segments enables other correction and variance options. In the preferred embodiment the electrode is radially segmented.

Radially segmented (pie-shaped) electrode arrangement works particularly well to cope with skin stretching induced artefacts. There is a physical and mathematical reason for that, based on strain analysis and underlying mechanical laws. FIG. 1 can be used as a graphical representation of a 2D state of strain subject to this invention.

The skin surface stretching is characterized by a planar bi-directional state of strain (or stress) in a small infinitesimal element of the electrode area or the full electrode area. Such a state deformation or strain is determined by two axial strains (Ex, Ey) and a shear strain (Exy), as shown in FIG. 1. Along the direction of so-called principal strains (minimum and maximum strain), the contribution of shear strain is zero. Due to biaxial strain state, we have two principal strains (E1 and E2); a compressive and a tensile one. The orientation of the principal strains can be calculated/determined by measuring axial and shear strains. These principal strains are orthogonally oriented to each other but under a certain angle with respect to an x-y coordinate system (or Ex and Ey). As principal strains always cross each other there must be directions along with skin deformation is more or less zero. According to Oborpta and Newman, the Finite strain ellipse (FIG. 1) can be used as a graphical representation of a 2D state of deformation and strain. From principal strains, one can mathematically derive associated lines of non-extension. From the principal strain directions the directions of non-extension can be calculated where Φ is the angle between the principal strain and LoNE direction (FIG. 1). Note that directions of non-extension only exist if compression and tension are both present. Mathematically this is when E1 and E2 have opposite signs. 102 indicate the direction of two lines of non-extension as deformed ellipse and undeformed circle intersect.

In a further embodiment the electrode forms concentric rings. Those embodiments are advantageous as the segments of electrode cover regions of the skin, where virtually no deformations occur.

Similarly to radially segmented electrode segments, concentric rings are used to be able to read out directions of intersecting zero skin deformation (lines of non extension; LoNE) which are the result of two principal strains.

The concept of deformation and motion of human skin states that deformations in an elastic body are described by a strain ellipsoid or ellipse (FIG. 1), in which a small sphere of material deforms to nearly ellipsoidal shape under elastic deformation of the entire body. On the surface of such an elastic body, the projected deformations transform a small circle into an ellipse. Since all points on the ellipse are derived from points on the undeformed circle, in general, there may be two directions in the ellipse that are not stretched. (They may be noted by superimposing the original circle on the deformed ellipse in FIG. 1) An extension and connection of these radial directions may be referred to as a mapping of the surface of the elastic body by lines of nonextension. Skin is a soft composite tissue with non-linear viscoelastic material properties and responds to body movement via skin stretching. During body movement the skin is stretched as skin layers are firmly connected with each other and via fascia, muscle and tendons attached to the skeleton. Therefore it is plausible to expect that skin stretching for example will cause changes in skin surface topography and surface strain distribution from which signal artefact can arise. There is no direct physical interaction between segments and skin stretching. The number of segments and geometry is pre-defined; though only segments associated with zero skin stretch are read out.

In a further embodiment the electrode comprise an skin adhering electrode layer made of hydrogel, hygroscopic silicone gel adhesive or other medical grade skin adhesive such as polyurethane gel, acrylic adhesive, hydrocolloid, and related pressure sensitive adhesive.

In a further embodiment the electrode comprise stretchable, flexible sheet of material. This embodiment is advantageous as it enables detecting a skin deformation, because the electrode can accommodate for skin-electrode strain mismatch and any deformation of the skin will result in a deformation of the sensor material which can be measured.

In a further embodiment each electrode segment comprises a conductive carbon-filled or conductive ionic (i.e., soap and carbon filled) silicone rubber (elastomer) and is further arranged to measure deformation and identify deformation free electrode segments. This embodiment is advantageous as it enables detecting a skin deformation by additionally integrating the deformation measurement function. Conductive silicone elastomer was developed by Philips and has been shown to be very sensitive for example for pressure measurement; therefore it may be also used as strain measurement technology. In a further embodiment the deformation sensor comprises a strain gauge, a fibre optic sensor or a magnetic sensor. The deformation sensing technologies can be resistive, capacitive, optical, inductive or magnetic. These measurement options all allow integration into the electrode.

In a further embodiment the deformation sensor senses the deformation in at least two dimensions.

In a further embodiment the processor is further arranged to process the deformation information based on a determination of the Line of Non-extension (LoNEs). The concept of the Lines of Non-extension was developed by Arthur Iberall during research on the space suite. He described the Line of Non-extension (LoNEs) as contours along the human body where the skin does not stretch.

As it was explained above intersecting zero skin deformation (lines of non extension LoNEs; there are typically 2 LoNE axes; see also FIG. 1) are the result of two principal strains arising from a biaxial strain condition skin is subjected to. The reason why skin has bi-axial strain state is because skin layers are firmly connected with each other and via fascia, muscle, tendons attached to the bone/skeleton. Electrode segments (electrode radially segmented and electrode form concentric rings) are used to be able to read out electrode segments associated with lines of non extension (LoNEs) and activate only these segments which lie on contours along the human body where the skin does not or only minimally stretch (LoNEs).

According to a second aspect of the invention, the objective is realized by a method for a vital sign monitoring. A method comprises: identification of a deformation of an electrode comprising multiple electrode segments by a deformation sensor, selecting at least one electrode segment that has lowest deformation of all electrode segments, measuring a vital sign signal using the selected electrode segment (or segments).

In various embodiments, the method may comprise selecting at least one electrode segment that has lowest deformation of all electrode segments associated with lines of non-extension, LoNEs, of the underlying soft skin tissue.

According to a third aspect, there is provided a vital sign monitoring system comprising a deformation sensor configured to identify deformation of a skin adhering electrode comprising multiple electrode segments and a processor configured to select an electrode segment that has a lowest deformation of all electrode segments associated with lines of non-extension, LoNEs, of the underlying soft skin tissue and measure a vital sign signal using the selected electrode segment.

According to a fourth aspect, there is a method of operating a vital sign monitoring system that comprises a segmented electrode forming an in-plane electrode array. The electrode comprises a skin adhering contact layer mounted on a skin facing side of the electrode. The method comprises identifying deformation information of the electrode, receiving a vital sign signal from the electrode and processing the deformation information to remove artefacts from the vital sign signal. The segmented electrode comprises multiple electrode segments. The method also comprises selecting the electrode segment that has a lowest deformation of all electrode segments of the electrode.

In various embodiments, the signal processor may be arranged to measure the vital sign signal using the selected electrode segment.

In various embodiments, the electrode may comprise either (semi-) rigid or stretchable, flexible sheet of material arranged to support the multiple electrode segments with respect to each other.

In various embodiments, the skin facing side of the electrode may comprise an electrode backing material. In various embodiments, the electrode backing material may comprise the multiple electrode segments. In various embodiments, the electrode may comprise either (semi-) rigid or stretchable, flexible sheet of material as the backing material.

BRIEF DESCRIPTION OF THE DRAWINGS

In the drawings, similar reference characters generally refer to the same parts throughout different views. Also, the drawings are not necessarily to scale, with the emphasis instead generally being placed upon illustrating the principles of the invention.

DETAILED DESCRIPTION OF EMBODIMENTS

Figure 1:
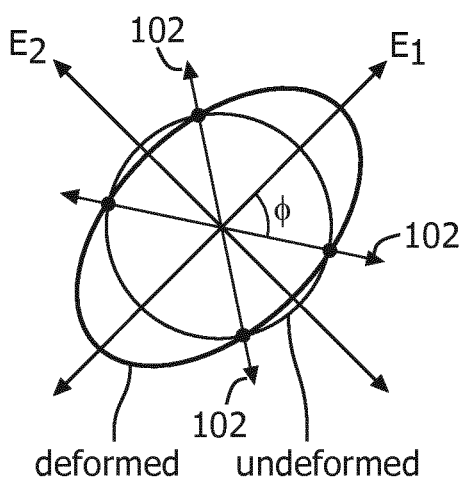
FIG. 1 shows a graphical representation of a 2D deformation state, based on the Finite Strain Ellipse method according to Obropta and Newman.

Certain embodiments will now be described in greater details with reference to the accompanying drawings. In the following description, like drawing reference numerals are used for like elements, even in different drawings. The matters defined in the description, such as detailed construction and elements, are provided to assist in a comprehensive understanding of the exemplary embodiments. In addition, well-known functions or constructions are not described in detail since they would obscure the embodiments with unnecessary detail. Moreover, expressions such as "at least one of", when preceding a list of elements, modify the entire list of elements and do not modify the individual elements of the list.

Figure 2:
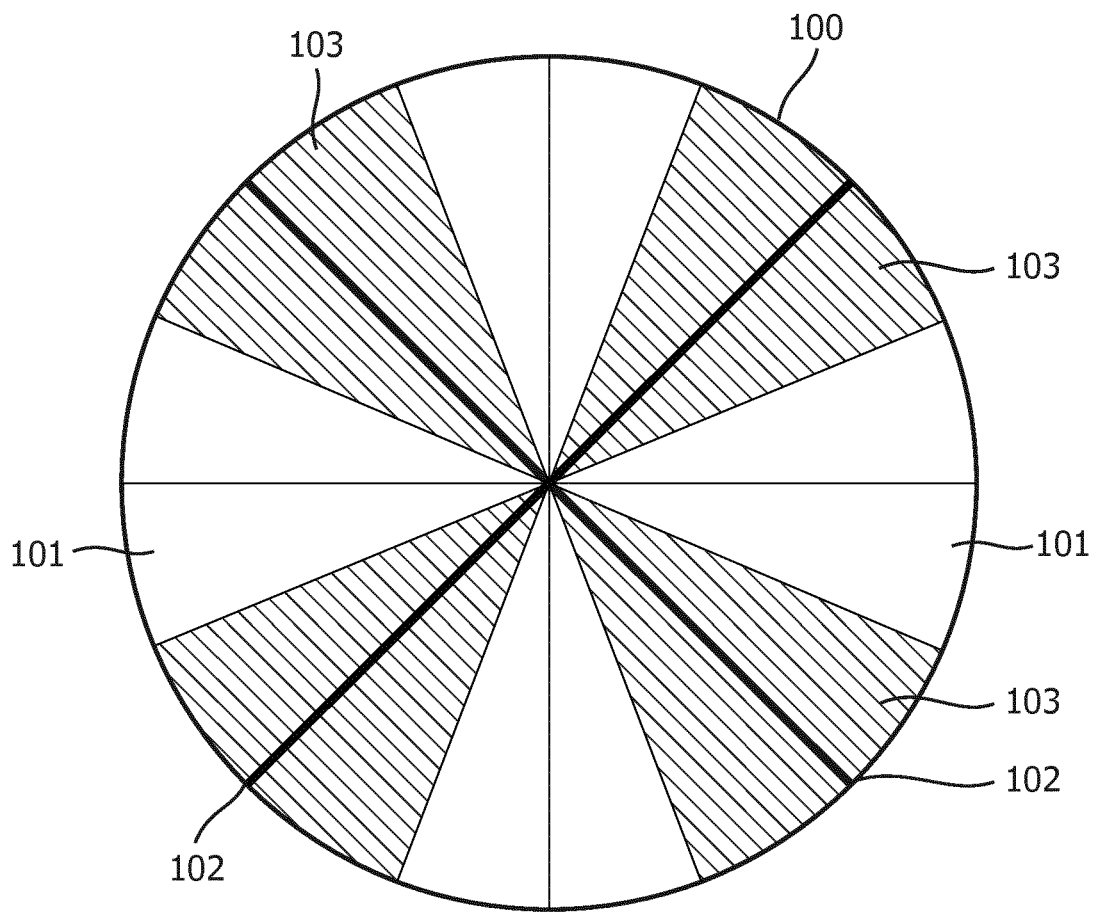
FIG. 2 shows a radially segmented (stretchable) electrode array and indicated example segments associated with Lines of Non-Extension.

FIG. 2 shows a radially segmented electrode sensor and two Lines of No Extension. In this example, an electrode 100 comprises 16 multiple radially arrayed electrode segments, whereas segments 101 indicate skin stretching affected ('deformed') and 103 skin stretching unaffected ('undeformed') segments (FIG. 2).

Although the human skin is stretched during body motion, there is virtually no stretch along the Lines of Non-extension (LoNEs) 102.

Since the human body tends to retain its form, taking no appreciable 'set' after ordinary body deformations, its behavior is expected to conform to the laws of physical elasticity. Deformations in an elastic body can be described by the strain ellipsoid, in which a small sphere of material deforms to nearly ellipsoidal shape under elastic deformation of the entire body. On the surface of such an elastic body, the projected deformations transform a small circle into an ellipse. Since all points on the ellipse are derived from points on the undeformed circle, in general, there may be two directions in the ellipse that are not stretched (They may be noted by superimposing the original circle on the deformed ellipse.) An extension and connection of these radial directions may be referred to as a mapping of the surface of the elastic body by lines of non-extension.

During a measurement, electrode segments 103 will experience little or no deformation as they are positioned along the Line of no extension 102 and the system will thus identify these as electrode segments that have a low deformation of all electrode segments and underlying skin. The electrode segment with the lowest deformation is subsequently selected by the system to obtain an optimised skin-stretching artefact removed vital sign signal.

Figure 6:
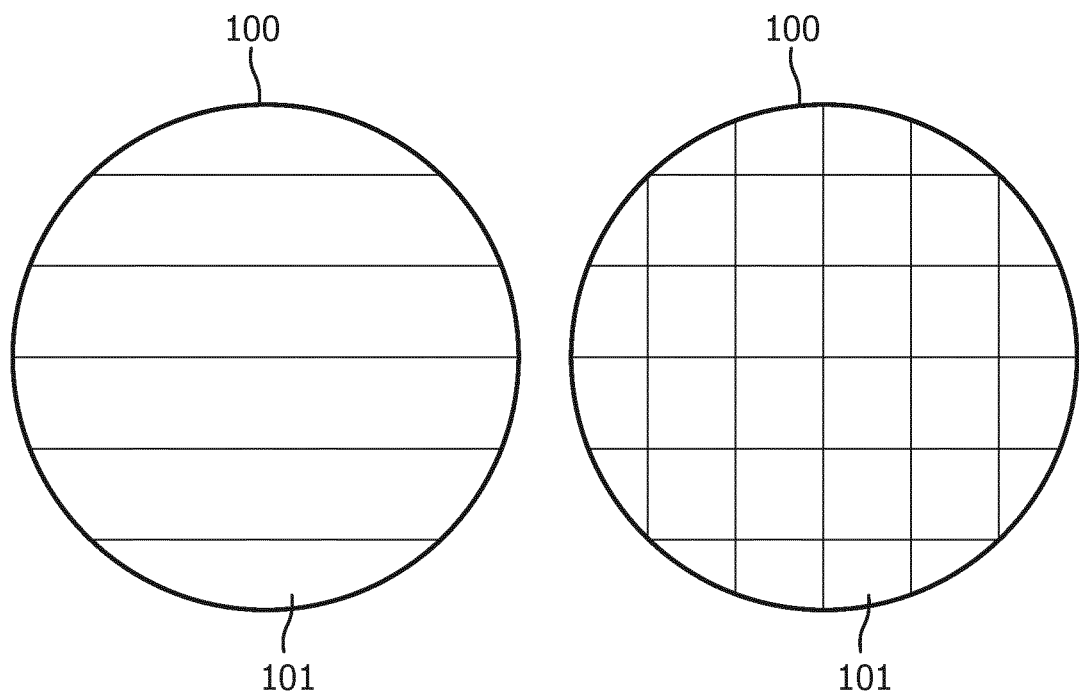
FIG. 6 shows a segmented (stretchable) electrode array electrode with longitudinal segments and a chessboard pattern.

Radially segmented electrode arrangement works particularly as they allow for greatest flexibility to read-out of segments associated with zero stretch (NoLE), because the angle between principal strains is normally unknown (and not constant throughout the skin or body) and needs to be measured for example with strain gauges. In a segmented electrode with longitudinal segments and a chessboard pattern (FIG. 6) only one read-out along one-line (one zero strain direction) would be accurate. In this case, the electrode does not need to be a of circle sector shape (radially arrayed) but can be designed also in other ways having straight lateral segments throughout the circle area.

Figures 3A, 3B:
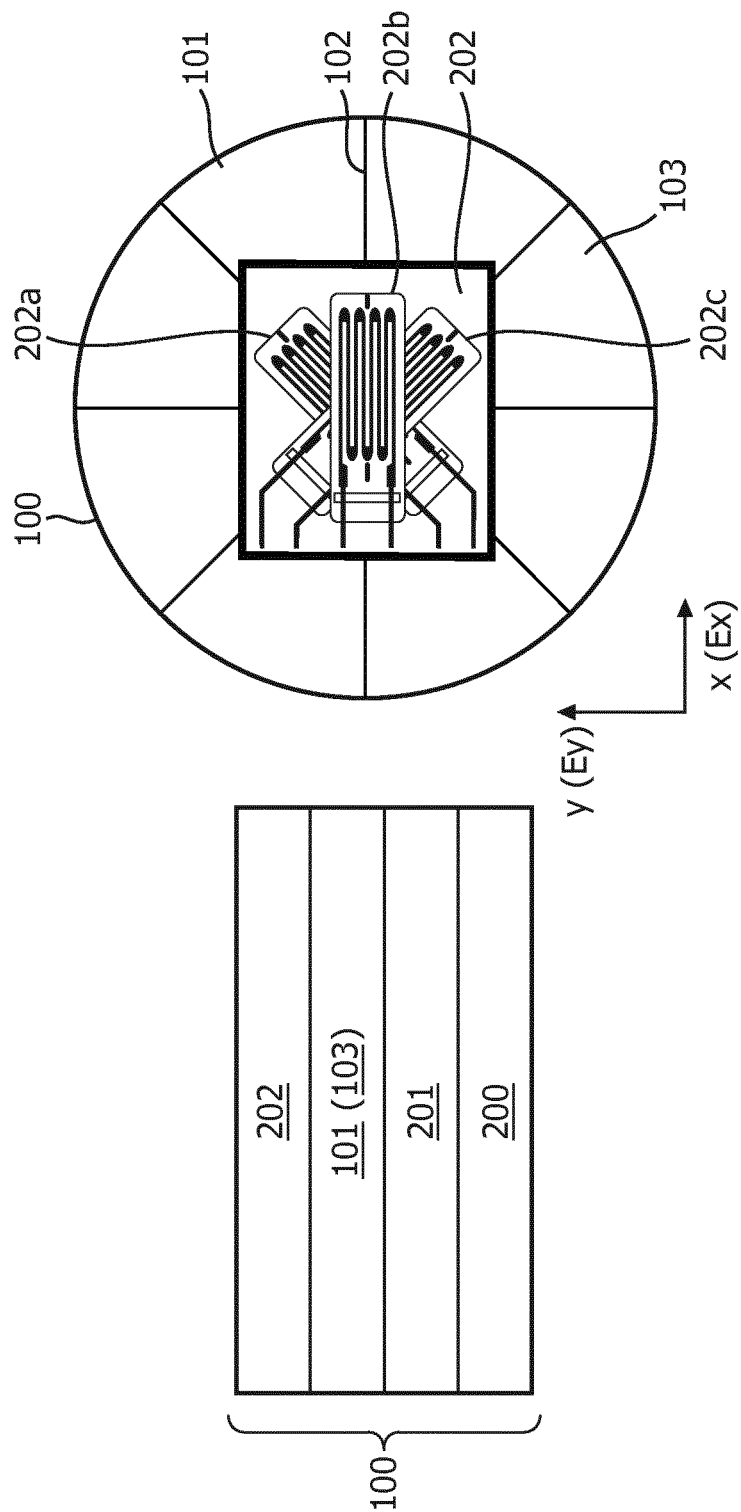
FIG. 3a shows a radially segmented sensor array having strain gauges incorporated therein.
FIG. 3b shows a cross section of the electrode according to the invention.

FIGS. 3 (*a* and *b*) depicts a radially segmented sensor having strain gauges incorporated therein. An electrode 100 comprises a stretchable radially segmented electrode with 8 segments 101(103) and a strain gauge sensor 202. The skin adhering electrode layer (100) is placed on the skin (200) of the patient and is maintained on the skin with an skin adhering electrode layer 201 as shown in FIG. 3*b*. The ideal electrode material (and encapsulation material of the strain gauge) is made of an elastic material to conform to the skin and matching the skin properties, i.e. one resembling the mechanical viscoelastic material behavior of skin. This can be for example a conductive ionic silicone membrane electrode onto which strain gauges are mounted to measure strains. Using suitable data acquisition and software algorithms and control loops (multiplexing) one can continuously measure strain indicated by the various strain gages and switch the measurement between electrode segments to adapt to changing skin deformations caused by (body motion, and read out that electrode segment where the lines of non-extension result in the least amount of deformation and thus a vital sign signal with the lowest amount of artefacts caused by skin deformation). Strain gauges 202 (202*a*, 202*b*, 202*c*) are placed on top of the stretchable electrode 101 (103). In a variant of this embodiment, the segments themselves can be used as strain (deformation) measurement system as a stretchable conductive carbon-filled silicone rubber (elastomer) is used as an electrode material so separate strain gauges or other deformation measurements means are no longer needed. In another variant of this embodiment, an array of meander-structure metal wires can be integrated in the bulk of the electrode and used as strain sensor.

There are at least 3 individual (separate) strain gauges 202*a*, 202*b*, 202*c*: two of the strain gauges should be placed at a 90 degree angle to each other as two orthogonal strains such as Ex and Ey should be measured. The third one can be chosen randomly as it measures a shear strain. If a rosette strain gauge is used, standardized configurations are chosen.

In FIG. 3*b* a cross section of the electrode according to the invention is shown. In this embodiment, strain gauges 202 are placed on top of the stretchable electrode 101(103). The skin adhering electrode layer (100) is placed on the skin (200) of the patient and is maintained on the skin with an adhesive 201.

Figure 4:
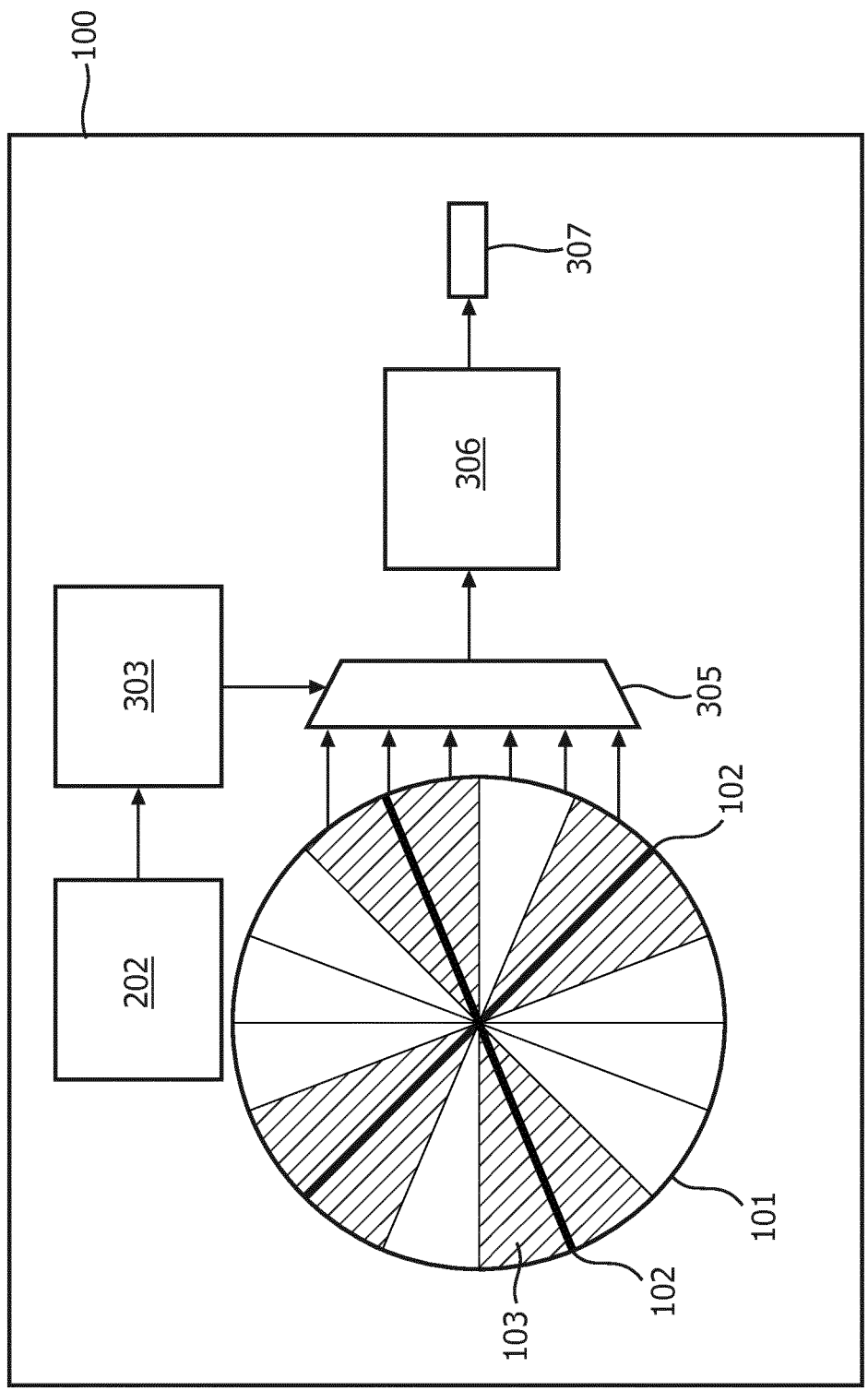
FIG. 4 shows a vital sign measurement system.

FIG. 4 depicts a vital sign measurement system showing a conceptual schematic describing the spatial selection of stretchable electrode segments 101 (103). As shown in this example, the system 100 contains 16 electrode segments 101. Each segment 101 is connected to an analog multiplexer 305 which is controlled by a processor 303 (typically a microcontroller). The processor 303 selects electrode segments 101 that are being measured by the read out electronics 306. The read out electronics comprises for instance sampling unit, amplification unit, and analog-to-digital conversion unit. The processor 303 estimates the deformation level applied to each electrode based on the deformation measurements obtained from the strain gauges 202 that are shown separately in FIG. 4 for clarity reasons but are actually as explained in FIG. 3, part of the electrode sensor 100. The electrode segment selection is then based on this estimation. The processor 303 can for example select each electrode showing a strain lower than a certain threshold value or select the one segment with the lowest deformation associated. The specific and number of electrode segments that are being selected can vary over time based on the deformation level variations that are being measured. The wearable device is therefore adapting its measurements based on the specific body movement.

If the deformation on each electrode segment 101 is unknown, it may still be possible to determine which of the segments are reporting reliable information based upon the fact that there are 2 LoNE axes. For this reason, if a sufficiently dense mesh of radial electrodes is defined (must be radially spaced by at most half the closest angle between 2 LoNE axes), then there should be 2 sets of radial electrode segments which qualitatively show the same or similar skin stretching artefact reduced biosignal output (all others should show deviating results). In addition, analysis may allow identification of an artefact as it is a component of the signal and varies from segment to segment, reaching a minimum in one of the electrode segments. The electrode segments thus found can be defined as the correct measurement. Again, criteria can be defined to reject measurements in situations where either difference between any 2 measurements exceeds a certain threshold or radial electrodes with the same result are too close together to form the 2 LoNE axes (i.e. if 2 adjacent electrodes indicate the same value).

In addition a calibration could be performed where the patient is asked to move through a series of motions while observing the resulting artefacts and identifying for the applied sensor which electrode segments are positioned at a Line of No Extension.

Figure 7:
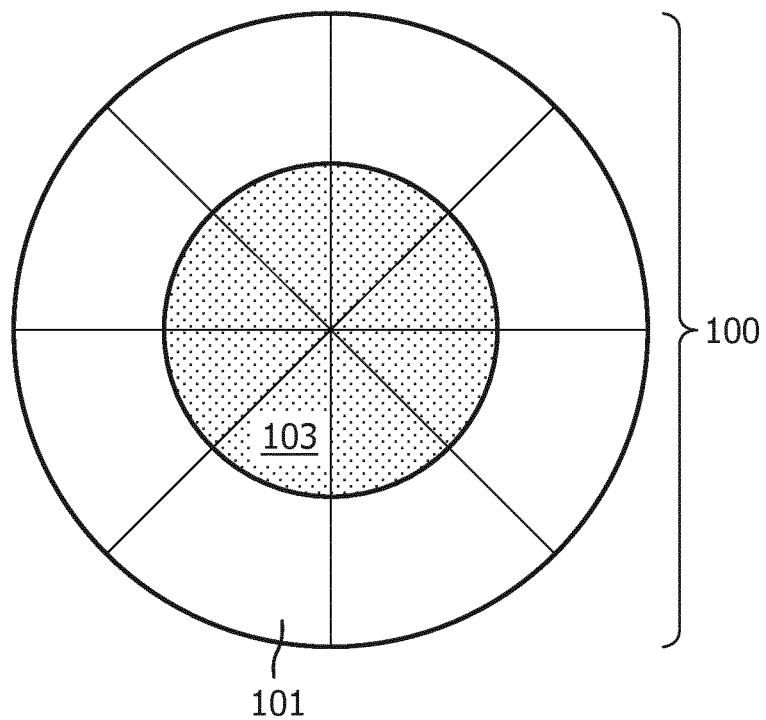
FIG. 7 shows a segmented (stretchable) electrode array, wherein electrode segments are concentric rings.

In a further embodiment, concentric rings of electrode segments (FIG. 7) are used in order to account for non-uniform strains. For example, the smaller the electrode segment (inner ring 103) the more likely that an area of low strain may be measured, however at a lower signal accuracy. A larger electrode segment delivers higher quality measurement but of course with a higher chance of artefacts introduced by deformation. Again, comparisons between smaller (103) and larger (101) electrode ring segments can considered.

Another embodiment of a vital sign monitoring system according to the present invention is a combination of the deformation measurement for example using a strain gauge with electrode segments output signals to make the identification of zero-stretch electrode segments more robust/reliable. An alternative to this embodiment is to exclude electrode segments with signal levels above a certain threshold (i.e. above typical physiological signal levels). This processing step should be applied after having filtered out common-mode interferences (e.g. 50/60 Hz).

Figure 5A:
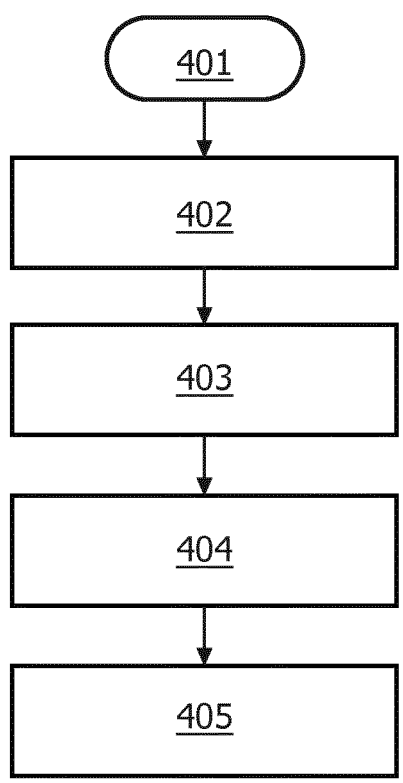
FIG. 5 shows a schematic representation of a method according to the present invention.
Figure 5B:
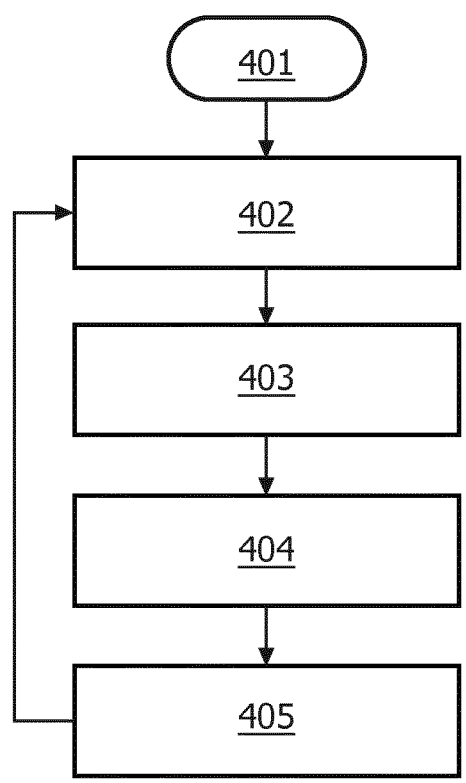

The method according to the invention is depicted in FIG. 5. Specifically, in FIG. 5*a* after beginning of the vital sign measurement in step 401 by the vital sign monitoring system, the next step 402 is the identification of a deformation of an electrode comprising multiple electrode segments by the system using a deformation sensor. Then in step 403 the system selects that electrode segment that has a lowest deformation of all the segments of that electrode and using the selected electrode segment start measuring a vital sign signal of the patient (404). Then subsequently the vital sign signal of the patient is stored (405). FIG. 5b shows alternative version of method according to invention. A loop from step 405 back to step 402 so that the deformation information is again obtained and the selection changed if another electrode segment turns out to be more optimal.

While several inventive embodiments have been described and illustrated herein, those of ordinary skill in the art will readily envision a variation of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

It should also be understood that, unless clearly indicated to the contrary, in any methods claimed herein that include more than one step or act, the order of the steps or acts of the method is not necessarily limited to the order in which the steps or acts of the method are recited. Also, reference numerals appearing in the claims in parentheses are provided merely for convenience and should not be viewed as limiting in any way.

The invention claimed is:

1. A vital sign monitoring system comprising:
an electrode forming an in-plane electrode array, wherein the electrode comprises a plurality of electrode segments and a skin adhering contact layer mounted on a skin facing side of the electrode;
a deformation sensor arranged for identifying deformation information indicating respective deformations of the plurality of electrode segments of the electrode; and
a signal processor programmed to receive a vital sign signal from the electrode, to process the deformation information to select an electrode segment of the plurality of electrode segments that has a lowest deformation of the plurality of electrode segments, and to measure the vital sign signal using the selected electrode segment to reduce artefacts from the vital sign signal.

2. The system of claim 1, wherein the electrode is radially segmented.

3. The system of claim 1, wherein the plurality of electrode segments form concentric rings.

4. The system of claim 1, wherein the electrode further comprises a skin adhering electrode layer made of hydrogel, hygroscopic silicone gel adhesive, a polyurethane gel, an acrylic adhesive, a hydrocolloid.

5. The system of claim 1, wherein the electrode further comprises a (semi-) rigid or stretchable, flexible sheet of material arranged to support the plurality of electrode segments with respect to each other.

6. The system of claim 1, wherein each electrode segment of the plurality of electrode segments comprises conductive carbon-filled silicone rubber and is arranged for identifying the deformation information.

7. The system of claim 1, wherein the deformation sensor comprises:
a strain gauge, a fibre optic sensor, a magnetic sensor, or a micro-camera.

8. The system of claim 1, wherein the deformation sensor senses the deformation of the electrode in at least two dimensions.

9. The system of claim 1, wherein the processor is further programmed to process the deformation information based on a determination of Lines of Non-extension (LoNEs).

10. A vital sign monitoring system comprising:
an electrode comprising a plurality of stretchable electrode segments and a skin adhering layer configured to adhere the electrode to skin of a patient;
a deformation sensor configured to determine deformations of the plurality of stretchable electrode segments of the electrode; and
a signal processor programmed to select at least one electrode segment of the plurality of stretchable electrode segments that has a lowest deformation of the plurality of electrode segments based on the determined deformations of the plurality of stretchable electrode segments, and to measure a vital sign signal indicating a vital sign of the patient using the at least one selected electrode segment.

11. The system of claim 10, wherein the plurality of stretchable electrode segments are radially segmented.

12. The system of claim 10, wherein the plurality of stretchable electrode segments comprise elastic material configured to conform to the skin of the patient and to match properties of the skin.

13. A method for a vital sign monitoring comprising:
identifying a deformation of a skin adhering electrode comprising a plurality of electrode segments by a deformation sensor, wherein the plurality of electrode segments are deformable;
selecting an electrode segment of the plurality of electrode segments that has a lowest deformation of the plurality of electrode segments associated with lines of non-extension (LoNEs) of underlying soft skin tissue; and
measuring a vital sign signal using the selected electrode segment.

14. The method of claim 13, wherein the electrode comprises a stretchable, flexible sheet of material.

15. The method of claim 13, wherein the electrode is radially segmented.

16. The method of claim 13, wherein the plurality of electrode segments are arranged in concentric rings.

17. The method of claim 13, wherein the plurality of electrode segments are arranged longitudinally.

18. The system of claim 1, wherein the plurality of electrode segments are arranged longitudinally.

19. The system of claim 1, wherein the plurality of electrode segments are arranged in a chessboard pattern.

20. The method of claim 13, wherein the plurality of electrode segments are arranged in a chessboard pattern.

* * * * *